United States Patent [19]

Dawson et al.

[11] Patent Number: 5,057,536

[45] Date of Patent: Oct. 15, 1991

[54] MACROLIDE COMPOUNDS

[75] Inventors: Michael J. Dawson, Ickenham; David Noble, Stoke Mandeville; Gordon C. Lawrence, Burnham; Richard A. Fletton, Ruislip; Stephen J. Lane, Eastcote; Michael V. J. Ramsay, South Harrow; Oswy Z. Pereira, Heston; Derek R. Sutherland, Chalfont St Giles; Edward P. Tiley, Village Way, all of England

[73] Assignee: American Cyanamid Company, Wayne, N.J.

[21] Appl. No.: 351,391

[22] Filed: May 9, 1989

[30] Foreign Application Priority Data

May 10, 1988 [GB] United Kingdom ................ 8811034
May 10, 1988 [GB] United Kingdom ................ 8811035

[51] Int. Cl.$^5$ .................. A61K 31/365; C07D 493/22
[52] U.S. Cl. ...................................... 514/450; 514/63; 549/264; 549/214
[58] Field of Search ................ 549/264, 214; 514/450, 514/63

[56] References Cited

U.S. PATENT DOCUMENTS

| | | | |
|---|---|---|---|
| 4,547,520 | 10/1985 | Ide et al. ........................ | 549/264 |
| 4,666,937 | 5/1987 | Goegelman et al. ............. | 549/264 |
| 4,831,016 | 5/1989 | Mrozik et al. .................. | 549/264 |
| 4,857,509 | 8/1989 | Frei et al. ...................... | 549/264 |

FOREIGN PATENT DOCUMENTS

| | | | |
|---|---|---|---|
| 0259686 | 3/1988 | European Pat. Off. ........... | 549/264 |
| 0259688 | 3/1988 | European Pat. Off. ........... | 549/264 |
| 0259779 | 3/1988 | European Pat. Off. ........... | 549/264 |

*Primary Examiner*—Richard L. Raymond
*Assistant Examiner*—Mark W. Russell
*Attorney, Agent, or Firm*—Bacon & Thomas

[57] ABSTRACT

Compounds of formula (1)

and salts thereof, wherein $R^1$ represents a methyl, ethyl or isopropyl group;
$Y^1$ is —$CH_2$—, $Y^2$ is —CH— and X represents $$-\overset{R^2\;\;R^3}{\underset{}{C}}-$$

where $R^2$ represents a hydrogen atom or a group $OR^8$ (where $OR^8$ is a hydroxyl group or a substituted hydroxyl group having up to 25 carbon atoms) and $R^3$ represents a hydrogen atom, or $R^2$ and $R^3$ together with the carbon atom to which they are attached represent >C=O, >C=$CH_2$ or >C=$NOR^9$ (where $R^9$ represents a hydrogen atom, a $C_{1-8}$ alkyl group or a $C_{3-8}$ alkenyl group) and the group >C=$NOR^9$ is in the E configuration] or —$Y^1$—X—$Y^2$— represents —CH=CH—CH— or —$CH_2$—CH=C—;

$R^4$ represents a group $OR^8$ as defined above and $R^5$ represents a hydrogen atom, or $R^4$ and $R^5$ together with the carbon atom to which they are attached represent >C=O or >C=$NOR^{9a}$ (where $R^{9a}$ is as defined above for $R^9$);

$R^6$ represents a hydrogen atom and R represents —$CH_2OH$, —CHO, —$CO_2H$ or a carboxylic acid ester or amide group; or $R^6$ represents a hydroxyl group and R represents a methyl group; and $R^7$ represents a hydrogen atom or when R represents a group —$CH_2OH$ then $R^7$ may also represent a hydroxyl group.

The compounds may be used to control nematode, acarine, insect or other pests.

10 Claims, No Drawings

MACROLIDE COMPOUNDS

This invention relates to novel macrolide compounds, to processes for their preparation and to compositions containing them.

UK Patent Specification 2166436 and European Patent Specification 170006 describe the production of a class of macrolides, designated S541 or LL-F28249. Derivatives of these compounds are for example described in UK Patent Specifications 2176182A and 2192630A. We have now found a further group of S541 compounds which have pesticidal activity as described below and also are useful as intermediates in the preparation of other S541 compounds.

Thus, according to one aspect of the present invention we provide the compounds of formula (1)

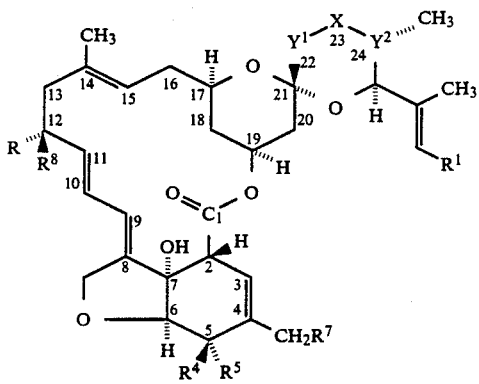

and salts thereof, wherein
$R^1$ represents a methyl, ethyl or isopropyl group;
$Y^1$ is —$CH_2$—, $Y^2$ is —CH— and X represents

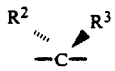

[where $R^2$ represents a hydrogen atom or a group $OR^8$ (where $OR^8$ is a hydroxyl group or a substituted hydroxyl group having up to 25 carbon atoms) and $R^3$ represents a hydrogen atom, or $R^2$ and $R^3$ together with the carbon atom to which they are attached represent >C=O, >C=$CH_2$ or >C=$NOR^9$ (where $R^9$ represents a hydrogen atom, a $C_{1-8}$ alkyl group or a $C_{3-8}$ alkenyl group) and the group >C=$NOR^9$ is in the E configuration] or -$Y^1$-X-$Y^2$- represents —CH=CH—CH— or —$CH_2$—CH=C—;
$R^4$ represents a group $OR^8$ as defined above and $R^5$ represents a hydrogen atom, or $R^4$ and $R^5$ together with the carbon atom to which they are attached represent >C=O or >C=$NOR^{9a}$ (where $R^{9a}$ is as defined above for $R^9$);
$R^6$ represents a hydrogen atom and R represents —$CH_2OH$, —CHO, —$CO_2H$ or a carboxylic acid ester or amide group; or $R^6$ represents a hydroxyl group and R represents a methyl group; and
$R^7$ represents a hydrogen atom or when R represents a group —$CH_2OH$, then $R^7$ may also represent a hydroxyl group.

When R represents a carboxylic acid ester group this may be, for example, a group —$CO_2R^{16}$ (where $R^{16}$ is an aliphatic, araliphatic or aromatic group, for example an alkyl, alkenyl, alkynyl, cycloalkyl aralkyl or aryl group).

When R represents a carboxylic acid amide group this may be, for example, a group —$CONR^{17}R^{18}$ (where $R^{17}$ and $R^{18}$ may each independently represent a hydrogen atom or a group as defined above for $R^{16}$).

The group $R^8$ when present in compounds of formula (1) may represent an acyl group e.g. a group of the formula $R^{10}CO$— or $R^{10}OCO$— or $R^{10}OCS$— (where $R^{10}$ is an aliphatic, araliphatic or aromatic group, for example an alkyl, alkenyl, alkynyl, cycloalkyl, aralkyl or aryl group), a formyl group, a group $R^{11}$ which is as defined above for $R^{10}$, a group $R^{12}SO_2$— (where $R^{12}$ is a $C_{1-4}$ alkyl or $C_{6-10}$ aryl group), a silyl group, a cyclic or acyclic acetal group, a group —$CO(CH_2)_nCO_2R^{13}$ (where $R^{13}$ is a hydrogen atom or a group as defined above for $R^{10}$ and n represents zero, 1 or 2) or a group $R^{14}R^{15}NCO$— (where $R^{14}$ and $R^{15}$ may each independently represent a hydrogen atom or a $C_{1-4}$ alkyl group).

Where $R^{10}$, $R^{11}$, $R^{16}$, $R^{17}$ or $R^{18}$ are alkyl groups, they may be for example $C_{1-8}$ alkyl groups, e.g. methyl, ethyl, n-propyl, i-propyl, n-butyl, i-butyl, t-butyl or n-heptyl which alkyl groups may also be substituted. $R^{10}$, $R^{16}$, $R^{17}$ and $R^{18}$ alkyl groups may be substituted by, for example, one or more, e.g. two or three, halogen atoms (e.g. chlorine or bromine atoms), or a carboxy, $C_{1-4}$ alkoxy (e.g. methoxy, ethoxy), phenoxy or silyloxy group. Where $R^{11}$ is a substituted alkyl group it may be substituted by a cycloalkyl e.g. cyclopropyl group.

Where $R^{10}$, $R^{11}$, $R^{16}$, $R^{17}$ and $R^{18}$ are alkenyl or alkynyl groups, they preferably have 2–8 carbon atoms and where they are cycloalkyl groups, they may be for example $C_{3-12}$ cycloalkyl, such as $C_{3-7}$ cycloalkyl, e.g. cyclopentyl groups.

Where $R^{10}$, $R^{11}$, $R^{16}$, $R^{17}$ and $R^{18}$ are aralkyl groups, they preferably have 1–6 carbon atoms in the alkyl moiety, and the aryl group(s) may be carbocyclic or heterocyclic and preferably contain 4–15 carbon atoms e.g. phenyl. Examples of such groups include phen $C_{1-6}$ alkyl e.g. benzyl groups.

Where $R^{10}$, $R^{11}$, $R^{16}$, $R^{17}$ and $R^{18}$ are aryl groups, they may be carbocyclic or heterocyclic and preferably have 4–15 carbon atoms e.g. phenyl.

When $R^8$ is a group $R^{12}SO_2$—, it may be for example a methylsulphonyl or p-toluenesulphonyl group.

Where $R^8$ represents a cyclic acetal group, it may for example have 5–7 ring members as in the tetrahydropyranyl group.

When $R^8$ represents a silyl group or $R^{10}$, $R^{16}$, $R^{17}$ or $R^{18}$ contains a silyloxy substituent, the silyl group may carry three groups which may be the same or different, selected from alkyl, alkenyl, alkoxy, cycloalkyl, aralkyl, aryl and aryloxy groups. Such groups may be as defined above and particularly include methyl, t-butyl and phenyl groups. Particular examples of such silyl groups are trimethylsilyl and t-butyldimethylsilyl.

When $R^8$ represents a group —$CO(CH_2)_nCO_2R^{13}$, it may for example be a group —$COCO_2R^{13}$ or —$COCH_2CH_2CO_2R^{13}$ where $R^{13}$ represents a hydrogen atom or a $C_{1-4}$ alkyl group (e.g. methyl or ethyl).

When $R^8$ represents a group $R^{14}R^{15}NCO$—, $R^{14}$ and $R^{15}$ for example may each independently be a hydrogen atom or a methyl or ethyl group.

When $R^9$ or $R^{9a}$ represents a $C_{1-8}$ alkyl group it may be for example a methyl, ethyl, n-propyl, i-propyl, n-butyl, i-butyl or t-butyl group, and is preferably a methyl group.

When $R^9$ or $R^{9a}$ represents a $C_{3-8}$ alkenyl group it may be for example an allyl group.

Compounds of formula (1) containing an acidic group may form salts with suitable bases. Examples of such salts include alkali metal salts such as sodium and potassium salts.

Compounds in which R is a carboxylic acid ester or amide are generally prepared on account of their activity. Where R represents a group $-CO_2R^{16}$, $R^{16}$ is preferably a $C_{1-8}$ alkyl group as defined above, particularly methyl. When R represents a group $-CONR^{17}R^{18}$, $R^{17}$ is preferably a hydrogen atom and $R^{18}$ is preferably a $C_{1-8}$ alkyl group as defined above, particularly n-butyl.

In the compounds of formula (1) $R^1$ preferably represents an isopropyl group.

An important group of compounds of formula (1) is that in which $Y^1$ is $-CH_2-$, $Y^2$ is $-CH-$ and X represents

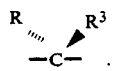

Particularly important compounds of this type are those in which $R^2$ is a hydrogen atom or a hydroxy, ethoxy or acetyloxy group and $R^3$ is a hydrogen atom or $R^2$ and $R^3$ together with the carbon atom to which they are attached represent $>C=O$, $>C=CH_2$ or $>C=NOCH_3$.

A further important group of compounds of formula (1) is that in which $R^4$ is a hydroxy, methoxy or acyloxy (e.g. acetyloxy) group or $R^4$ and $R^5$ together with the carbon atom to which they are attached represent $>C=NOCH_3$. $R^4$ preferably represents a hydroxy group.

Important active compounds according to the invention are those of formula (1) in which:

R represents a group $-CO_2CH_3$, $R^1$ is an isopropyl group, $Y^1$ is $-CH_2-$, $Y^2$ is $-CH-$, X represents $>CNOCH_3$, $R^4$ is a hydroxyl group and $R^5$ is a hydrogen atom; and R represents a group $-CONH(CH_2)_3CH_3$, $R^1$ is an isopropyl group, $Y^1$ is $-CH_2-$, $Y^2$ is $-CH-$, X represents $>CNOCH_3$, $R^4$ is a hydroxyl group and $R^5$ is a hydrogen atom.

R is a group $-CO_2H$, $R^1$ is an isopropyl group, $Y^1$ is $-CH_2-$, $Y^2$ is $-CH-$, X represents $>C=NOCH_3$, $R^4$ is a hydroxy group and $R^5$, $R^6$ and $R^7$ are hydrogen atoms.

Compounds of formula (1) in which R is $-COOH$ are particularly useful as intermediates in the preparation of other formula (1) compounds.

As indicated previously, compounds of the invention have antibiotic activity e.g. antihelminthic activity, for example against nematodes, and in particular, anti-endoparasitic and anti-ectoparasitic activity.

The antibiotic activity of the compounds of formula (I) may, for example, be demonstrated by their activity against parasitic nematodes such as *Nematospiroides dubius* and *Caenorhabditis elegans*.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

Furthermore, the compounds of formula (I) are also of use in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti*.

According to the invention we therefore provide the compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or other vegetation) or to the pests themselves or a locus thereof.

The compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds of formula (I) may be formulated for use in veterinary or human medicine according to the general methods described in UK Patent Specification 2166436.

The total daily dosages of the compounds of the invention employed in both veterinary and human medicine will suitably be in the range 1–2000 μg/kg bodyweight, preferably from 50–1000 μg/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers and diluents are as described in UK Patent Specification 2166436.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The rate at which a compound is applied depends upon a number of factors including the type of pest involved and the degree of infestation. However, in general, an application rate of 10 g/ha to 10 kg/ha will be suitable; preferably from 1 g/ha to 10 kg/ha for control of mites and insects and from 50 g/ha to 10 kg/ha for control of nematodes.

For use in veterinary medicine or for horticultural and agricultural use it may be desirable to use whole fermentation broth, as a source of the active compound. It may also be suitable to use dried broth (containing mycelia) or to use mycelia separated from the broth and pasteurised or more preferably, dried e.g. by spray-, freeze-, or roller drying. If desired the broth or mycelia may be formulated into compositions including conventional inert carriers, excipients or diluents as described above.

The antibiotic compounds of the invention may be administered or used in combination with other active ingredients.

In particular, the antibiotic compound of the invention may be used together with other antibiotic compounds. This may occur, for example, where whole fermentation broth is used without prior separation of compounds of the invention or where crude fermentation products are reacted according to the fermentation process of the invention without prior or subsequent separation; this may be preferable for example in agricultural use of a compound, where it is important to maintain low production costs.

The compounds according to the invention may be prepared by a number of processes as described in the following where $R^1, R^4, R^5, R^6, R^7, X, Y^1$ and $Y^2$ are as defined for general formula (1) unless specified otherwise. In some of these processes it may be necessary to protect one or more of any hydroxyl groups present in the starting material prior to effecting the reaction described. In such cases it may then be necessary to deprotect the same hydroxyl group(s) once the reaction has occurred to obtain the desired compound of the invention. Conventional methods of protection and deprotection may be used, for example, as described in 'Protective Groups in Organic Synthesis' by Theodora W. Greene (Wiley-Interscience, New York 1981) and 'Protective Groups in Organic Chemistry' by J. F. W. McOmie (Plenum Press, London 1973). Thus, for example, an acyl group such as an acetyl group may be removed by basic hydrolysis e.g. using sodium hydroxide or potassium hydroxide or ammonia in an aqueous alcohol such as methanol.

Thus, according to another aspect of the invention, we provide a process for preparing a compound of formula (1) (in which $R^6$ is a hydrogen atom and R is —CH$_2$OH, —CHO or —COOH, or $R^6$ is —OH and R is —CH$_3$) which comprises incubating a compound of formula (2)

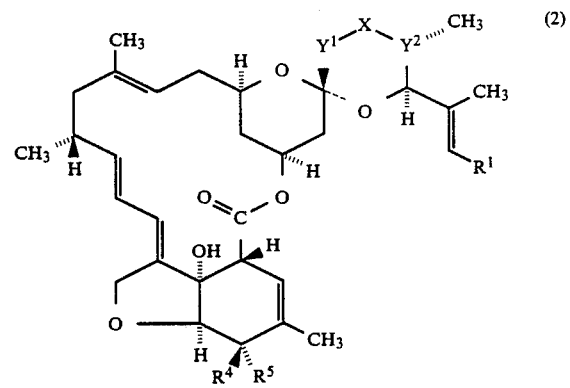

in a suitable medium in the presence of a microorganism or an enzyme derived therefrom or a preparation derived from a microorganism containing the enzyme of interest capable of effecting the conversion.

Suitable microorganisms and extracts thereof for use in the process according the invention may be identified by preliminary small scale tests designed to demonstrate ability of a microorganism or an extract thereof to convert compounds of formula (2) to compounds of formula (1). The formation of the compounds of formula (1) may be confirmed by suitable chromatographic analysis (e.g. high performance liquid chromatography) of the reaction mixture.

We have found microorganisms of the genus Streptomyces and extracts thereof to be particularly suitable for use in the process according to the present invention.

Particular Streptomyces microorganisms for use in the process according to the invention include strains of *Streptomyces griseoplanus, Streptomyces virginiae, Streptomyces cacaoi, Streptomyces spinichromogenes* var. *kujimyceticus, Streptomyces tendae, Streptomyces aureofaciens, Streptomyces autotrophicus, Streptomyces filamentosus, Streptomyces canescens, Streptomyces deltae, Streptomyces fungicidicus* var. *espinomyceticus, Strep-* tomyces mycarofaciens, Streptomyces rimosus, Streptomyces djakartensis, Streptomyces mashuensis and Streptomyces platensis subsp malvinus, and mutants of these strains.

Particularly suitable Streptomyces microorganisms for use in the process according to the invention include strains of *Streptomyces mashuensis, Streptomyces rimosus* and *Streptomyces platensis* subsp. *malvinus* e.g. *Streptomyces mashuensis* ISP 5221, *Streptomyces rimosus* NRRL 2455 and *Streptomyces platensis* subsp. *malvinus* NRRL 3761 and mutants thereof.

Mutants of the above strains may arise spontaneously or may be produced by a variety of methods including those described in UK Patent Specification 2166436.

Other bacteria which may be used include *Pseudomonas putida, Pseudomonas aeruginosa, Pseudomonas fluorescens, Pseudomonas oleovarans, Mycobacterium rhodochrous, Micrococcus flavoroseus, Aerobacter aerogenes* and *Corynebacterium simplex*.

Other microorganisms which may be used in the process according to the invention include fungi and plant cell preparations.

Examples of particular fungi for use in the process according to the invention include *Penicillium oxalicum, Rhizopus nigricans, Calonectria decora, Aspergillus ochraceus, Cunninghamella elegans, Rhizopus arrhizus, Giberella fujikuroi, Absidia orchidis, Absidia cylindrospora, Cunninghamella blakesleeana, Cunninghamella echinulata, Mucor hiemlis, Cladosporium herbarum, Curvularia lunata, Pellicularia filamentosa, Aspergillus fumigatus, Aspergillus niger* and *Fusarium oxysporum*.

Example of plant cell preparations for use in the process according to the invention include *Phaseolus vulgaris* L., *Citrus paradisi, Nicotiana tabacum* L., *Coptis japonica, Digitalis purpurea* and *Dioscorea tokoro*. Plant cell preparations are particularly useful in the process according to the invention for making compounds of formula (1) in which R is a group —CH$_2$OH.

The bioconversion may also be effected using an organism containing the genetic material of one of the aforementioned microorganisms that participates in the synthesis of the compound of formula (1). Such organisms may be obtained using genetic engineering techniques including those outlined by D. A. Hopwood in 'Cloning genes for Antibiotic Biosynthesis in Streptomyces Spp.: Production of a hybrid antibiotic' p 409–413 in Microbiology 1985, Ed. L. Lieve, American Society of Microbiology, Washington D.C. 1985. Such techniques may be used in a similar manner to that described previously for cloning antibiotic biosynthetic genes, including the biosynthetic genes for actinorhodin (Malpartida, F. and Hopwood, D. A. 1984, Nature 309, p 462–464), erythromycin (Stanzak, R. et al, 1986, Biotechnology, 4, p 229–232) and an important enzyme involved in penicillin and cephalosporin production in *Acremonium chrysogenum* (Sansom, S. M. et al, 1985, Nature, 318, p 191–194).

Suitable enzymes for use in the process accoding to the present invention may be derived from an extremely wide range of sources. The aforementioned Streptomyces microorganisms, however, represent a particularly suitable source of enzymes capable of converting compounds of formula (2) into compounds of formula (1).

In one embodiment of the process according to the invention, the conversion of a compound of formula (2) into a compound of formula (1) may be effected by feeding the compound of formula (2) e.g. in a suitable solvent into a fermentation medium comprising the aforementioned microorganism in the presence of assimilable sources of carbon, nitrogen and mineral salts. Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean meal, corn steep liquors, distillers solubles, yeast extracts, cottonseed meal, peptones, ground nut meal, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient mineral salts which may be incorporated into the culture medium include the generally used salts capable of yielding sodium, potassium, ammonium, iron, magnesium, zinc, nickel, cobalt manganese, vanadium, chromium, calcium, copper, molybdenum, boron, phosphate, sulphate, chloride and carbonate ions.

An antifoam may be present to control excessive foaming and added at intervals as required.

The compound of formula (2) in a solvent such as a water miscible organic solvent (e.g. an alcohol such as methanol or propan-2-ol, a diol such as propan-1,2-ol or butan-1,3-ol, a ketone such as acetone, a nitrile such as acetonitrile, an ether such as tetrahydrofuran or dioxan, a substituted amide such as dimethylformamide or a dialkylsulphoxide such as dimethylsulphoxide) may be added at the beginning of the cultivation, or more usually, when the growth of the microorganism is under way, e.g. 2 to 4 days after the start of the cultivation.

Cultivation of the organism will generally be effected at a temperature of from 20° to 50° C., preferably from 25° to 40° C., and will desirably take place with aeration and agitation e.g. by shaking or stirring. The medium may initially be inoculated with a small quantity of a suspension of the sporulated microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 4.0 to 9.5, preferably 5.5 to 8.5 when a Streptomyces organism is used and preferably 4.0 to 8.5 when other bacteria or a fungus are used.

Once the compound of formula (2) has been added to the culture, usually with gentle mixing, the cultivation is continued such that the desired product is accumulated. The presence of the product in the fermentation broth may be determined by monitoring extracts of the broth by high performance liquid chromatography, and uv spectroscopy at 238 nm.

The product(s) may be isolated from the whole fermentation broth by conventional isolation and separation techniques as described in UK Patent Specifications 2166436 and 2176182.

When plant cells are used as part of the fermentation process it is preferable for the cultivation to be carried out using a plant medium containing a plant cell growth regulator such as indole acetic acid, naphthalene acetic acid, indole butyric acid, 2,4-dichlorophenoxyacetic acid, kinetin or benzylamino purine at a temperature of from 15° to 35° C. with the pH maintained within the range 5.0 to 7.5. Ammonium salts and nitrates also constitute the preferred sources of nitrogen present in the fermentation medium. Sucrose, fructose and glucose also constitute the preferred sources of carbon present in the fermentation medium.

In a further embodiment of the process according to the invention, the conversion of a compound of formula (2) into a compound of formula (1) may be effected by combining and incubating a compound of formula (2) e.g. in a suitable solvent (e.g. a water miscible organic solvent as previously defined) with a preparation of the enzyme of the invention, desirably in a buffer solution, at, for example, 0° to 60°, preferably 20° to 40° e.g. about 28° C. The reaction will generally be carried out in the pH range 3.5 to 8.5 e.g. 5.5 to 7.5. If desired the reaction may be carried out in the presence of a cofactor such as NADH or NADPH. When the reaction is complete, i.e. when the compound of formula (2) is no longer converted to the compound of the invention (as determined by monitoring extracts of the reaction mixture by high performance liquid chromatography and uv spectroscopy at 238 nm) the product is recovered by conventional isolation and separation techniques as described in UK Patent Specifications 2166436 and 2176182.

The enzyme for use in the process of the present invention may be prepared, for example, by culture of a microorganism which produces the enzyme in a nutrient medium. Suitable nutrient media and fermentation conditions for the preparation of the enzyme include those previously described for the preparation of a compound of formula (1) from a compound of formula (2) in the presence of a microorganism. The time at which the required enzymic activity reaches a maximum will, of course, vary according to the microorganism used and, hence, the optimum cultivation time is desirably determined independently for each strain employed.

For microorganisms where the enzyme is extracellular, the liquid culture medium or the filtrate after removal of whole cells may be used as a source of enzyme. Where the enzyme is cell-bound it may be released for use by conventional methods such as sonication, grinding with glass beads, homogenisation, treatment with lytic enzymes or with detergents, after suspension of the cells in a suitable buffer.

The resulting preparation, either with or without removal of cell debris, may be used as a source of enzyme. It is preferred, however, to purify the enzyme further by conventional means. Batch or column chromatography with ion-exchange celluloses or affinity adsorbents or other adsorbents e.g. hydroxylapatite may conveniently be employed. In addition, the enzyme may be concentrated or further purified by molecular sieve techniques e.g. ultrafiltration or salting out. In general, during purification procedures, it is desirable to maintain the pH within the range 3 to 11.

The enzyme may be employed in an immobilized form, e.g. by insolubilisation or entrappment thereof on or in a suitable matrix. Thus an extract of the enzyme may be bound or linked to an otherwise inert inorganic or organic polymer, entrapped on or in a fibre, or on or in a membrane or polymer such as polyacrylamide gel, adsorbed on an ion-exchange resin, crosslinked with a reagent such as glutaraldehyde, or occluded in an envelope such as a bead. Immobilized enzymes may advantageously be employed both in batch processes, after which the enzyme may be reused, and continuous flow processes wherein substrates pass through a column containing the immobilized enzyme.

Compounds of formula (1) in which R represents a carboxylic acid ester group may be prepared by treating a corresponding carboxylic acid of formula (1) in which R is —COOH or a salt thereof or a reactive derivative thereof, such as an acid halide (e.g. acid chloride or anhydride), with a reagent capable of effecting the conversion to the corresponding esters of formula (1) and, if desired, followed by removal of any 5- and/or 23-hydroxyl protecting groups present.

Suitable esterification conditions include standard literature procedures. Thus, for example, esterification may be effected using an alcohol e.g. an alcohol of the formula $R^8OH$ (where $R^8$ is as previously defined).

Esterifications employing alcohols may desirably be conducted in the presence of a condensing agent, for example, a carbodiimide such as N,N'-dicyclohexylcarbodiimide. An acid binding agent such as a tertiary amine (e.g. triethylamine, dimethylaniline, pyridine or 4-pyrrolidino pyridine) may also be present.

Esterification of a compound of formula (2) to prepare a compound of formula (1) in which R represents a group —$CO_2R^8$ (where $R^8$ is an alkyl, e.g. tert-butyl, group) may also be effected using an alkene such as isobutylene with the reaction carried out at elevated pressure.

Esterification of a compound of formula (2) to prepare a compound of formula (1) in which R represents a group —$CO_2R^8$ (where $R^8$ is a methyl group) may also be effected using diazomethane.

Esterification may conveniently be effected in a solvent such as an ether (e.g. diethyl ether, tetrahydrofuran or dioxan), a ketone (e.g. acetone), an amide (e.g. N,N-dimethylformamide), a nitrile (e.g. acetonitrile), a hydrocarbon such as a halogenated hydrocarbon (e.g. methylene chloride) or an ester (e.g. ethyl acetate), as well as mixtures of two or more such solvents. Alternatively, when an alcohol is employed this may also be used as the solvent for the reaction. The esterification reaction may conveniently be carried out at a temperature in the range −20° to +100° C. e.g. −10° to +50° C.

According to another aspect of the invention, we provide a process (B) for preparing a compound of formula (1) in which R represents a carboxylic acid amide group which comprises treating the parent carboxylic acid or a salt thereof or a reactive derivative thereof with a suitable amine e.g. an amine of the formula $R^{17}R^{18}$ NH (where $R^{17}$ and $R^{18}$ are as previously defined).

The reaction may be effected in a suitable solvent e.g. a halogenated hydrocarbon such as dichloromethane at around 20° C. A suitable condensing agent such as 1-ethoxycarbonyl-2-ethoxy-1,2-dihydroquinoline may also conveniently be present.

In a further process, the compounds of formula (1) in which $OR^8$ is a substituted hydroxyl group may generally be prepared by reacting the corresponding 5- and-/or 23-hydroxy compound with reagent serving to form a substituted hydroxyl group.

The reaction will in general be an acylation, sulphonylation, etherification, silylation or acetalation, and the reaction may be carried out according to the general methods described in UK Patent specification 2176182.

In yet a further process, the compounds of formula (1) in which $R^4$ and $R^5$ together with the carbon atom to which they are attached represent $>C=O$ may be prepared by oxidation of the corresponding 5-hydroxy compounds in which $R^4$ is a hydroxyl group.

The reaction may be effected with an oxidising agent serving to convert an allylic secondary hydroxyl group to an oxo group, whereby a compound of formula (1) is produced.

Suitable oxidising agents include, for example, transition metal oxides, such as manganese dioxide, and atmospheric oxygen in the presence of a suitable catalyst such as a finely divided metal e.g. platinum.

The oxidising agent will generally be used in excess over the stoichiometric quantity.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate. Combinations of such solvents either alone or with water may also be used.

The reaction may be carried out at a temperature of from $-50°$ C. to $+50°$ C., preferably from $0°$ to $30°$ C.

In another process according to the invention a compound of formula (1) in which X represents the group $>C=NOR^9$ and $R^4$ is a group $OR^8$ or $R^4$ and $R^5$ together with the carbon atom to which they are attached represent $>C=O$, or X represents

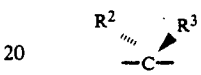

(where $R^2$ is a hydrogen atom or a group $OR^8$ and $R^3$ is a hydrogen atom or $R^2$ and $R^3$ together with the carbon atom to which they are attached represent $>C=NOR^9$) or $-Y^1-X-Y^2-$ represents $-CH=CH-CH-$ or $-CH_2-CH=C-$ and $R^4$ and $R^5$ together with the carbon atom to which they are attached represent $>C=NOR^{9a}$ may be prepared from the corresponding 5 and/or 23-keto compounds of formula (1) by reaction with a reagent $H_2NOR^9$ (where $R^9$ is as previously defined).

The oximation reaction may conveniently be effected at a temperature in the range $-20°$ to $+100°$ C., e.g. $-10°$ to $+50°$ C. It is convenient to use the reagent $H_2NOR^9$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosphoramide), ethers (e.g. cyclic cyclic ethers such as tetrahydrofuran or dioxan, and acylic ethers such as dimethoxyethane or diethylether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

It will be appreciated that when the compounds of formula (1) in which X represents $>C=NOR^9$ and $R^4$ and $R^5$ together with the carbon atom to which they are attached represent $>C=NOR^{9a}$ are prepared from the corresponding 5,23-diketones (i.e. compounds of formula (1) in which X represents $>C=O$ and $R^4$ and $R^5$ together with the carbon atom to which they are attached represent $>C=O$) the groups $>C=NOR^9$ and $>C=NOR^{9a}$ will be the same.

In a further process according to the invention a compound of formula (1) in which X represents the group $>C=O$ may be prepared by oxidising a compound of formula (1) in which X represents

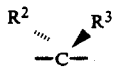

(wherein $R^2$ is a hydroxyl group and $R^3$ is a hydrogen atom). The reaction may be effected with an oxidising agent serving to convert a secondary hydroxyl group to an oxo group, whereby a compound of formula (1) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl chloride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used.

The reaction may be carried out at a temperature of from $-80°$ C. to $+50°$ C.

In another process according to the invention a compound of formula (1) in which X represents $>C=CH_2$ may be prepared by reacting the corresponding 23-keto compounds (i.e. compounds of formula (1) in which X represents $>C=O$) with an appropriate Wittig reagent e.g. a phosphorane of formula $(R^a)_3P=CH_2$ (where $R^a$ is $C_{1-6}$ alkyl or aryl e.g. monocyclic aryl such as phenyl). Suitable reaction solvents include ethers such as tetrahydrofuran or diethyl ether or a dipolar aprotic solvent such as dimethylsulphoxide. The reaction may be carried out at any suitable temperature e.g. at $0°$.

In a further process, a compound of formula (1) in which X is $-CH_2-$ may be prepared by treating a corresponding compound in which $R^2$ is a hydroxyl group and $R^3$ is a hydrogen atom sequentially with (i) oxalyl chloride and (ii) 2-mercaptopyridine-N-oxide, a catalytic amount of an organic base e.g. a tertiary amine such as dimethylaminopyridine and a thiol which is preferably a hindered thiol e.g. trityl thiol.

The reaction may be carried out in an inert solvent such as an aromatic hydrocarbon e.g. toluene. Stage (i) may conveniently be carried out at room temperature and stage (ii) at an elevated temperature e.g. reflux.

In a yet further process according to the invention a compound of formula (1) in which -$Y^1$-X-$Y^2$ represents —CH=CH—CH— or —$CH_2$—CH=C— may be prepared by eliminating HL from a compound of formula (3) in which L is an eliminatable group, such as a group $OR^8$ (where $OR^8$ is a hydroxy or acyloxy group). The elimination reaction to yield a compound of formula (1) may be effected using conventional techniques, for example, as described in European Patent Specification 215654.

Salts of acids of formula (1) may be prepared by conventional methods, for example by treating the acid with a base or converting one salt into another by exchange of ion.

Intermediate compounds of formula (2) in which $Y^1$ is —$CH_2$—, $Y^2$ is —CH— and X represents

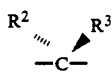

(where $R^2$ represents a hydrogen atom or a group $OR^8$ and $R^3$ represents a hydrogen atom or $R^2$ and $R^3$ together with the carbon atom to which they are attached represent >C=O) or -$Y^1$-X-$Y^2$- represents —CH=CH—CH— or —$CH_2$—CH=C— are either known compounds described in UK Patent Specifications 2166436 and 2176182 and European Patent Specification 215654 or may be prepared from such known compounds using procedures as described above.

Intermediate compounds of formula (2) in which $Y^1$ is —$CH_2$—, $Y^2$ is —CH— and X represents >C=$CH_2$ or >C=$NOR^9$ may be prepared from known compounds of formula (2) described in UK Patent Specifications 2166436 and 2176182 using the processes described above (for the preparation of corresponding compounds of formula (1)) and in UK Patent Specification 2192630 and European Patent Specification 231104).

The invention is further illustrated by the following Examples wherein the compound of formula (2) above in which $R^1$ is isopropyl, $Y^1$ is —$CH_2$—, $Y^2$ is —CH—, X represents

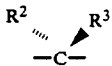

(where $R^2$ is a hydroxyl group and $R^3$ is a hydrogen atom), $R^4$ is a hydroxyl group and $R^5$ is a hydrogen atom is referred to as 'Factor A'. Compounds according to the invention are named with respect to Factor A. All temperatures are in °C.

EXAMPLE 1

12-Demethyl-Factor A 12-carboxylic acid

Sterile water (5 ml) was added to a slope of *Streptomyces platensis* subsp. *malvinus* NRRL 3761 and 1 ml portions used to inoculate 250 ml shake flasks containing the medium A (25 ml):

|  | $gL^{-1}$ |
|---|---|
| D-Glucose | 2.5 |

-continued

|  | $gL^{-1}$ |
|---|---|
| Malt Dextrose MD30E | 25.0 |
| Arkasoy 50 | 12.5 |
| Molasses | 1.5 |
| $KH_2PO_4$ | 0.125 |
| Calcium carbonate | 1.25 |
| [3-(N-Morpholino)propanesulphonic acid] | 21.0 |
| Distilled water | as required | pH adjusted to 6.5 with $H_2SO_4$ before autoclaving.

The flasks were incubated at 28° for 2 days on a rotary shaker (250 rpm) and this 2 day old culture (100 ml) was used to inoculate a 7 L fermenter containing Medium A (5 L). Incubation was continued at 28° with aeration (2 L/min) and stirring (250 rpm) and, after 2 days, a solution of Factor A (2.5 g) in dimethylsulphoxide (50 ml) was added. The fermentation was continued for a further 5 days, and the cells removed by centrifugation and extracted with the methanol. The aqueous supernatant, after removal of the cells, was extracted with ethyl acetate and the combined ethyl acetate extracts were added to the methanol extract and evaporated to give an oil. The oil was dissolved in water and the solution (160 ml) was washed with ether and extracted with ethyl acetate. The combined ethyl acetate extracts were evaporated and the residue dissolved in acetonitrile (15 ml), clarified by centrifugation and then applied to a column of Spherisorb S5 ODS-2 (250 mm × 20 mm) with detection at 240 nm as 1 ml portions diluted with an equal volume of acetonitrile/0.1M ammonium dihydrogen phosphate (1:1). Acetonitrile/0.1M ammonium dihydrogen phosphate (1:1) was used as eluent at a constant flow rate of 25 ml/min and the peak eluting between 14 and 17 min. was successively collected. All such fractions were combined, diluted with an equal volume of water and pumped back onto the column. The column was eluted with acetonitrile, the acetonitrile removed in vacuo and the residual solid dissolved in acetone, diluted with cyclohexane and lyophilised to yield the title compound (148 mg) as a colourless solid.

$^1$H N.m.r. ($CDCl_3$, 200 MHz) gave signals at about δ0.79 (d7, 3H), 0.94 (d7, 3H), 1.04 (d7, 3H), 1.52 (s, 3H), 1.59 (s, 3H), 1.84 (s, 3H), 3.23 (m, 2H), 3.73 (d11, 1H), 3.92 (d6, 1H), 4.27 (d6, 1H), 5.08 (t8, 1H) and 5.18 (d9, 1H); i.r. ($CHBr_3$ solution) 1702, 1730 and 3480 $cm^{-1}$; mass spectrum (E.I) gave an M+ ion at m/z 642 and fragment ions at m/z 624, 606, 560, 514, 512, 496, 478, 455, 437, 384, 344, 297, 278, 265, 247, 237, 219, 181, and 95; $^{13}$C n.m.r. (25.05 MHz) gave signals at about δ10.8(q), 13.7(q), 14.8(q), 19.6(q), 22.6(q), 26.6(d), 34.6(t), 35.7(d), 40.5(t), 42.5(t), 45.3(d), 46.6(d), 67.3(d), 67.6(d), 68.0(t), 69.1(d), 76.5(d), 79.1(d), 80.0(s), 99.5(s), 117.6(d), 119.3(d), 122.4(d), 127.3(d), 130.2(s), 132.5(d), 134.2(s), 137.2(s), 137.4(s), 141.7(s), 173.0(s) and 177.1(s).

EXAMPLE 2

12-Demethyl-23-keto Factor A 12-carboxylic acid

23-Keto Factor A (721 mg, Example 21 in UK Patent Specification 2176182) in methanol (50 ml) was added to a culture developed according to the method described in Example 1 above. The fermentation was continued under the same conditions for a further 2 days and the cells removed by centrifugation. The supernatant was adjusted to pH 2.0 with concentrated hydrochloric acid and extracted with ethyl acetate. The ethyl acetate extract was evaporated to give an oil which was dissolved in water (100 ml) containing sodium bicarbonate (2 g). The solution was washed with ether, adjusted to pH 2.0 and extracted with ether. The combined ether extracts were evaporated to an oily solid which was dissolved in methanol (4 ml), diluted in acetonitrile/0.1M ammonium dihydrogen phosphate (1:1, 0.7 ml) and filtered.

The resulting solution was applied to a column of Spherisorb S5 ODS-2 (250 mm × 20 mm) as 1.75 ml portions with detection of the fractions at 255 nm. Acetonitrile/0.1M ammonium dihydrogen phosphate (1:1) was used as eluent at a constant flow rate of 25 ml/min and the detected peaks eluting between 12.2 and 14.9 min from separate injections were combined, diluted with an equal volume of water and pumped back onto the column. The column was washed with acetonitrile/water (1:3) and eluted with acetonitrile. Evaporation of the acetonitrile followed by lyophilisation of the residue from acetone/cyclohexane yielded the title compound (258 mg) as a colourless solid. $^1$H N.m.r. (CDCl$_3$, 200 MHz) includes signals at about δ0.86 (d7, 3H), 0.96 (d7, 3H), 1.05 (d7, 3H), 1.52 (s, 3H), 1.70 (s, 3H), 1.87 (s, 3H), 3.25 (m, 2H), 3.70 (d11, 1H), 3.94 (d6, 1H), 4.28 (d6, 1H), 5.06 (t8, 1H) and 5.20 (d10, 1H); i.r. (Nujol) 1720, 3450 cm$^{-1}$; Mass spectrum (E.I.) gave an M+ ion at m/z 640 and fragment ions at m/z 622, 604, 579, 517, 499, 400, 356, 263 and 95.

EXAMPLE 3

12-Demethyl-23[E]-methoxyimino Factor A 12-carboxylic acid

The product of Example 2, methoxyamine hydrochloride (12.5 g) and sodium acetate (20.7 mg) in methanol (0.5 ml) were stirred for 16 h, and then diluted with dichloromethane and washed with water (25 ml) and brine. Evaporation of the dried organic phase afforded a foam which was dissolved in chloroform:methanol:acetic acid (180:8:1) and applied to a column of Merck Kieselgel 60, 230–400 mesh silica (25 g). Elution of the column with the same solvent system, under pressure, gave the title compound (62 mg), $[\alpha]_D^{21}$ +49° (c 0.4, CHCl$_3$), $\lambda_{max}^{EtOH}$ 248.2 nm (εmax 26,000), νmax (CHBr$_3$) 3470 (OH), 1740 (CO$_2$H) and 1708 cm$^{-1}$ (lactone), δ(CDCl$_3$) includes 0.92 (d,6 Hz,3H), 0.97 (d,6 Hz,3H), 1.07 (d,6 Hz,3H), 1.87 (s,3H), 3.2–3.4 (m,3H), 3.83 (s,3H), 3.96 (d,6 Hz,3H), and 4.29 (d,6 Hz,3H).

EXAMPLE 4

12a-Hydroxy-23-keto Factor A 25 ml of medium A in a 250 ml shake flask was inoculated directly from a slope of Streptomyces platensis subsp. malvinus NRRL 3761 and incubated at 28° on a rotary shaker (250 rpm, 2" throw) for 2 days. 5 ml aliquots of this 2 day old culture were transferred to 50 ml shake flasks and 50 μl of 23-keto Factor A in methanol (50 mg/ml) was added to give an input of 500 mg/L. The fermentation was continued under the same conditions for a further 3 days. An equal volume of methanol was then added and the shake flask and contents shaken for 1 h before centrifugation.

The supernatant was evaporated to dryness and the residue extracted with acetonitrile/0.05M ammonium acetate adjusted to pH 4.5 with acetic acid. The extract was clarified and the supernatant fractionated in 200 μl portions on a column of Spherisorb S5 ODS-2 (100 mm × 4.6 mm) with detection at 238 nm. A gradient eluting system was used, acetonitrile/0.05M ammonium acetate at pH 4.5 (40:60→60:40), at a constant flow rate of 3 ml/min and the peak eluting after 4.3 min. after each injection was successively collected. All such fractions were combined and evaporated to yield the title compound as a solid. Mass spectrum (E.I.) gave an M+ ion at m/z 626 and fragment ions at m/z 608, 565, 498, 455, 437, 386 and 167.

EXAMPLE 5

12a-Hydroxy Factor A

Factor A (2.5 g) in methanol (50 ml) was added to a culture of Streptomyces mashuensis ISP 5221 developed according to the method described in Example 1 above. The fermentation was continued under the same conditions for a further 5 days and the cells removed by centrifugation. The cells were combined with methanol and, after 30 min., centrifuged to give 900 ml of methanol extract. The supernatant from the culture fluid was extracted with ethyl acetate, the combined ethyl acetate extracts evaporated and the residue dissolved in the methanol extract from the cells. This mixture was evaporated, the residue dissolved in methanol (200 ml) and loaded onto a column of Sephadex LH20 (125 cm × 5 cm) eluting with methanol. Each 30 ml fraction was collected and fractions 47–57 were combined and evaporated. The residue was dissolved in acetonitrile/water (1:1, 10 ml) and purified by preparative high performance liquid chromatography on a column of Spherisorb S5 ODS-2 (250 mm × 20 mm) eluting with acetonitrile/water (1:1) at a rate of 20 ml/min with detection at 250 nm. Consecutive 1.5 ml portions were loaded onto the column and the peaks eluting between 14.8 and 15.6 min. were combined, diluted with an equal volume of water, pumped back onto the column and eluted with acetonitrile. Evaporation of the acetonitrile followed by lyophilisation from acetone/cyclohexane gave the title compound (25.1 mg) as a colourless solid. I.r. (CHBr$_3$) 996, 1710 and 3500 cm$^{-1}$; $^{13}$C n.m.r. (62.5 MHz) gave signals at about δ10.8 (q), 13.7 (q), 15.4 (q), 19.7 (q), 22.7 (q), 26.7 (d), 34.7 (t), 35.9 (d), 36.0 (t), 40.6 (t), 41.0 (t), 42.1 (t), 44.3 (d), 45.5 (d), 66.2 (t), 67.5 (d), 67.7 (d), 68.3 (t), 69.1 (d), 76.6 (d), 79.2 (d), 80.1 (s), 99.6 (s), 117.8 (d), 119.7 (d), 120.9 (d), 127.2 (d), 130.5 (s), 135.9 (s), 137.1 (d), 137.3 (d), 137.8 (s), 140.9 (s) and 173.2 (s); $^1$H n.m.r. corresponds with the spectrum for the corresponding product of Example 6.

EXAMPLE 6

12a-Hydroxy Factor A and 4a,12a-dihydroxy Factor A

Factor A (2.5 g) in methanol (50 ml) was added to a culture of Streptomyces rimosus NRRL 2455 developed according to the method of Example 1 above. The fermentation was continued under the same conditions for a further 5 days and the cells removed by centrifugation. The supernatant was discarded and the cells were washed with water and centrifuged again. The water wash was discarded, the cells were extracted with methanol and centrifuged again to give a methanol extract of 1300 ml. The methanol extract was evaporated to give an oil which was extracted with acetonitrile (250 ml) and methanol (200 ml). The extracts were combined and evaporated to give an oil which was dissolved in methanol (200 ml) and fractionated (50 ml) on a column of Sephadex LH20 (130 cm × 5 cm) eluting with methanol. Fractions 26 to 36 were combined and evaporated and the residue dissolved to acetonitrile/water (55:45, 15 ml) and 1.8 ml portions were subjected to preparative high performance liquid chromatography on a column of Spherisorb S5 ODS-2 (250 mm × 20 mm). The developing solvents were acetonitrile/water (55:45, 0 to 12.5 min.), acetonitrile/water (70:30, 12.5 to 21.0 min) and acetonitrile (21.0 to 30 min) which were applied at a rate of 20 ml/min. The column was then equilibrated with acetonitrile/water (55:45). The fractions eluting between 14.8 and 15.5 min. were collected, combined, diluted with an equal volume of water and pumped back onto the column. The column was eluted with acetonitrile and the acetonitrile removed. The residue was dissolved in acetone/cyclohexane and lyophilised to give 12a-hydroxy Factor A (32.2 mg) as a colourless solid. $^1$H n.m.r. (250 MHz, CDCl$_3$) includes signals at about δ0.80 (d6, 3H), 0.96 (d6, 3H), 1.06 (d6, 3H), 1.88 (s, 3H), 3.27 (m, 1H), 3.40 (t9, 1H), 3.74 (d11, 1H), 3.96 (d6, 1H), 4.30 (t6, 1H), 5.02 (m, 1H) and 5.21 (d9, 1H); mass spectrum (E.I.) gave an M+ ion at m/z 628 and fragment ions at m/z 610, 592, 482, 464, 441, 423, 370, 330, 297, 265, 247, 237, 219, 167 and 95.

Similarly, fractions eluting between 6.2 and 6.8 minutes gave 4a,12a-dihydroxy Factor A (26.4 mg) as a colourless solid. $^1$H N.m.r. (250 MHz, CDCl$_3$) includes signals at about δ0.80(d6; 3H), 0.96(d6; 3H) 1.06(d6; 3H), 1.56(s; 3H), 1.62(s; 3H), 3.31(m; 1H) 3.40(dd 11, 9; 1H), 3.75(d10; 1H), 3.97(d6; 1H), 4.24(d14; 1H), 4.33(d14; 1H), 4.58(d6; 1H) and 5.72(s; 1H).

Mass spectrum (E.I.) gave an M+ ion at m/z 644 and fragment ions at 626, 608, 482, 464, 457, 439, 297, 265, 247, 237, 219 and 167.

EXAMPLE 7

12-Hydroxy Factor A

Factor A (2.5 g) in methanol (50 ml) was added to a culture of *Absidia cylindrospora* NRRL 2796 developed according to the method of Example 1 except that the following medium was used:

|  | gL$^{-1}$ |
| --- | --- |
| Corn steep liquer | 20.0 |
| Meritose | 10.0 |
| Soya oil | 1.0 |
| Distilled water | as required | pH adjusted to 4.8-5.0 with potassium hydroxide before autoclaving.

The fermentation was continued under the same conditions for a further 5 days and the cells removed by centrifugation. The cells were then extracted with methanol (400 ml).

The supernatant from the culture fluid was evaporated down to about 900 ml and extracted with ethyl acetate. The combined ethyl acetate extracts were evaporated and the residue dissolved in methanol (ca. 100 ml). The resulting suspension was filtered and the filtrate evaporated to dryness.

The methanolic cell extract was evaporated to an oil which was dissolved in water and extracted with ethyl acetate. The combined ethyl acetate extract was then added to the supernatant residue and the mixture dried.

The residue was dissolved in chloroform/ethyl acetate (3:1, ca. 30 ml) and loaded onto a column of silica (100 ml, 70-230 mesh) containing a layer of sand. Each 20 ml fraction was collected and fractions 11-32 were combined and evaporated to dryness. The residue was purified by preparative high performance liquid chromatography on a column of Spherisorb S5 ODS-2 eluting with acetonitrile/water (1:1) at a rate of 30 ml/min with detection at 238 nm. Peaks eluting between 29.6 and 31.6 min were combined, diluted with an equal volume of water, pumped back onto the column and eluted with acetonitrile. The eluate was evaporated, the residue dissolved in acetone/cyclohexane and lyophilised to give the title compound (42.4 mg). $^1$H N.m.r. (250 MHz, CDCl$_3$) gave signals at about δ0.79(d7; 3H), 0.96(d7; 3H), 1.06(d6; 3H), 1.30(s; 3H), 1.60(s; 3H), 1.69(s; 3H), 1.89(s; 3H), 3.29(m; 1H), 3.75(d10; 1H), 3.98(d6; 1H), 4.30(t6; 1H), 5.41(s; 1H), 5.66(d15; 1H).

Mass spectrum (E.I.) gave an M+ ion at m/z 628 and fragment ions at 610, 592, 574, 484, 441, 423, 370, 334, 316, 265, 247, 237, 219 and 167.

EXAMPLE 8

12-Demethyl-Factor A 12-carboxylic acid, methyl ester (i) A solution of the product of Example 1 (100 mg), N,N'-dicyclohexylcarbodiimide (35 mg) and methanol (11 μl) in ether (2 ml) was stirred for 2½ h in the presence of a catalytic amount of 4-pyrrolidino pyridine (2 mg). The resulting mixture was filtered and the filtrate evaporated to a foam. Chromatographic purification of the foam on Merck Kieselgel 60 (25 g) afforded the title compound (31 mg) as a white foam, $[\alpha]_D^{21}$ +23° (c 0.5, CHCl$_3$), $\lambda_{max}^{EtOH}$ 245.6 nm (εmax 25,200), νmax (CHBr$_3$) 3500 (OH) and 1720 cm$^{-1}$ (CO$_2$R), δ(CDCl$_3$) includes 0.80 (d,6 Hz, 3H), 0.96 (d,6 Hz,3H), 1.06 (d,6 Hz,3H), 1.89 (s,3H), 3.25 (m,2H), 3.68 (s,3H), 3.96 (d,6 Hz,1H) and 4.29 (d,6 Hz,1H).

(ii) A stirred solution of Example 1 (155 mg) in ether (15 ml), at 0°-5°, was treated with excess ethereal diazomethane. After 30 min excess diazomethane was destroyed with acetic acid and the resulting colourless solution evaporated to yield a foam. Chromatographic purification of the foam on Merck Keiselgel 230-400 mesh silica (26 g) afforded the title compound (125 mg). The nmr spectrum was similar to that described above.

EXAMPLE 9

12-Demethyl-Factor A 5-acetate 12-carboxylic acid, methyl ester

A solution of the product of Example 8 (60 mg) and acetic anhydride (10.3 μl) in dry pyridine (1 ml) was stirred for 72 h. A catalytic portion of 4-dimethylamino pyridine (3 mg) was then added. After 20 min, the solution was diluted with ethyl acetate (60 ml) and washed sequentially with 2N hydrochloric acid, water and brine. Drying and evaporation of the organic phase afforded a foam which as a solution in hexane:ethyl acetate (2:1) was applied to a column of Merck Kieselgel 230-400 mesh silica (36 g). Elution of the column, under pressure, with the same solvent system yielded the title compound (35 mg) as a white foam, $[\alpha]_D^{21}$ +50° (c 0.4, CHCl$_3$), $\lambda_{max}^{EtOH}$ 239.4 nm (εmax 22,000), νmax (CHBr$_3$) 3480 (OH), 1730 (CO$_2$R+OCOCH$_3$) and 1235 cm$^{-1}$, δ(CDCl$_3$) includes 0.80 (d,6 Hz,3H), 0.96 (d,6 Hz,3H), 1.06 (d,6 Hz,3H), 1.74 (s,3H), 2.16 (s,3H), 3.24 (m,1H), 3.66 (s,3H), 4.06 (d,6 Hz,1H) and 5.53 (m,2H).

EXAMPLE 10

12-Demethyl-Factor A 12-carboxylic acid, isopropyl ester

A mixture of the product of Example 1 (150 mg), N,N'-dicyclohexylcarbodiimide (53 mg), dry isopropyl alcohol (176 μl) and a catalytic amount of 4-pyrrolidino pyridine (3.4 mg) was stirred for 26 h. The insoluble material was filtered, and the filtrate evaporated to a foam. The foam was dissolved in ether and washed with 5% aqueous acetic acid water and brine. Drying and evaporation of the organic phase afforded a foam which was purified by flash chromatography over silica (36 g) to give the title compound (53 mg), $\lambda_{max}^{EtOH}$ 245.6 nm (εmax 26,200), νmax (CHBr$_3$) 3500 (OH) and 1714 cm$^{-1}$ (CO$_2$R), δ(CDCl$_3$) includes 0.80 (d,6 Hz, 3H), 0.96 (d,6 Hz,3H), 1.07 (d,6 Hz,3H), 1.20 (d,6 Hz,6H), 1.87 (s,3H), 3.17 (m,1H), 3.96 (d,6 Hz,1H), 4.29 (t,6 Hz,1H), and 4.97 (m,1H).

EXAMPLE 11

12-Demethyl-Factor A 12-carboxylic acid, tert-butyl ester

A solution of Example 1 (500 mg) in ether (10 ml) was cooled to −30° and treated with concentrated sulphuric acid (30 μl) followed by isobutylene (30 ml). The resulting mixture was stirred at 21° in a sealed pressure bottle for 96 h. Excess isobutylene was allowed to evaporate and the ethereal residue diluted with dichloromethane (20 ml) and then washed sequentially with saturated sodium bicarbonate (20 ml), water (2×20 ml) and brine. Drying and evaporation of the organic phase gave a foam which, as a solution in dichloromethane:acetone (10:1), was applied to a column of Merck Keiselgel 230–400 mesh silica (68 g). Elution of the column under pressure with the same solvent system afforded the title compound (86 mg), as a white foam, $\lambda_{max}^{EtOH}$ 245.8 nm (εmax 28,600) νmax (CHBr$_3$) 3500 (OH) and 1712 cm$^{-1}$ (CO$_2$R), δ(CDCl$_3$) includes 0.80 (d,6 Hz,3H), 0.96 (d,6 Hz,3H), 1.06 (d,6 Hz,3H), 1.41 (s,9H), 1.89 (s,3H), 3.11 (m,1H), 3.97 (d,6 Hz,1H) and 4.29 (d,6 Hz,1H).

EXAMPLE 12

12-Demethyl-Factor A 5,23-bisacetate 12-carboxylic acid, methyl ester

A solution of the product of Example 8 (55 mg) in dry pyridine (2 ml) was treated with 4-dimethylamino pyridine (10 mg) followed by acetic anhydride (0.15 ml). After 80 h the solution was diluted with ethyl acetate (60 ml) and washed sequentially with 2N hydrochloric acid, saturated aqueous sodium bicarbonate, water and brine. Drying and evaporation of the organic phase yielded a foam which as a solution in hexane:ethyl acetate (2:1) was applied to a column of Merck Kieselgel 60, 230–400 mesh silica (16 g). Elution of the column under pressure with the same solvent system afforded the title compound (51 mg) as a white foam, $[\alpha]_D^{21}$+102° (c 0.4, CHCl$_3$), $\lambda_{max}^{EtOH}$ 245 nm (εmax 25,300), νmax (CHBr$_3$) 3460 (OH), 1728 (CO$_2$R and acetoxy) and 1258 and 1238 cm$^{-1}$ (OCOCH$_3$), δ(CDCl$_3$) includes 0.70 (d,6 Hz,3H), 0.95 (d,6 Hz,3H), 1.06 (d,6 Hz,3H), 1.74 (s,3H), 2.02 (s,3H), 2.16 (s,3H), 3.23 (m,1H), 3.67 (s,3H), 4.05 (d,5H,1H) and 5.52 (m,2H).

Examples 13 and 14 were prepared in a similar manner.

EXAMPLE 13

12-Demethyl-Factor A 5,23-bisacetate 12-carboxylic acid, isopropyl ester (26 mg) as a white foam, δ(CDCl$_3$) includes 0.70 (d,6 Hz,3H), 0.95 (d,6 Hz,3H), 1.07 (d,6 Hz,3H), 1.21 (d,6 Hz,6H), 1.77 (s,3H), 2.03 (s,3H), 2.17 (s,3H), 3.18 (m,1H), 4.06 (d,6 Hz,1H), 4.97 (m,1H), and 5.53 (m,2H), from the product of Example 10 (37 mg).

EXAMPLE 14

12-Demethyl-Factor A 5,23-bisacetate 12-carboxylic acid, tert-butyl ester (86 mg), $\lambda_{max}^{EtOH}$ 246.0 nm (εmax 26,500), νmax (CHBr$_3$), 1720 (CO$_2$R) and 1254 and 1235 cm$^{-1}$ (acetate), δ(CDCl$_3$) includes 0.71 (d,7 Hz,3H), 0.95 (d,6 Hz,3H), 1.06 (d,6 Hz,3H), 1.43 (s,9H), 1.76 (s,3H), 2.05 (s,3H), 2.17 (s,3H), 3.10 (m,1H), 4.07 (d,6 Hz,1H), 4.90 (q,3 Hz,1H) and 5.53 (m,2H) from the product of Example 11 (96 mg) except that the solution was diluted with dichloromethane (30 ml) before work-up.

EXAMPLE 15

12-Demethyl-Factor A 23-acetate 12-carboxylic acid, methyl ester

A solution of the product of Example (30 mg) in methanol (1 ml) was cooled to 0°–5° and treated with 1N sodium hydroxide (44 μl). After 3 h, the solution was diluted with ether (50 ml) and washed with 2N hydrochloric acid, water and brine. Drying and evaporation of the organic phase gave a foam. Flash chromatography of the foam over silica (16 g), using hexane:ethyl acetate (1:1) as eluent afforded the title compound (18 mg) as a white foam, $[\alpha]_D^{21}$+44° (c 0.2, CHCl$_3$), $\lambda max_{max}^{EtOH}$ 245.6 nm (εmax 32,500), νmax (CHBr$_3$) 3550 (OH), 3450 (OH), and 1720 cm$^{-1}$ (CO$_2$R), δ(CDCl$_3$) includes 0.70 (d,6 Hz,3H), 0.96 (d,6 Hz,3H), 1.07 (d,6 Hz,3H), 1.88 (s,3H), 2.03 (s,3H), 3.26 (m,2H), 3.67 (m,3H), 3.96 (d,6 Hz,1H), 4.29 (t,6 Hz, 1H), 4.90 (q,3 Hz,1H).

Examples 16 and 17 were prepared in a similar manner.

EXAMPLE 16

12-Demethyl-Factor A 23-acetate 12-carboxylic acid, isopropyl ester (15 mg), $[\alpha]_D^{21}$+71° (c 0.2, CHCl$_3$), $\lambda_{max}^{EtOH}$ 245.6 nm (εmax 27,500), νmax (CHBr$_3$) 1718 (CO$_2$R) and 1255 cm$^{-1}$ (acetate), δ(CDCl$_3$) includes 0.71 (d,6 Hz,3H), 0.96 (d,6 Hz,3H), 1.07 (d,6 Hz,3H), 1.22 (d,6 Hz,6H), 1.88 (s,3H), 2.03 (s,3H), 3.18 (m,1H), 3.97 (d,6 Hz,1H), 4.29 (t,6 Hz,1H), 4.90 (q,3 Hz,1H), 4.98 (m,1H), from the product of Example 13 (24 mg).

EXAMPLE 17

12-Demethyl-Factor A 23-acetate 12-carboxylic acid, tert-butyl ester (46.5 mg) as a white foam $[\alpha]_D^{21}$+54° (c 0.4, CHCl$_3$), $\lambda_{max}^{EtOH}$ 246 nm (εmax 25,200), νmax (CHBr$_3$) 1710 (CO$_2$R) and 1250 cm$^{-1}$ (acetate), δ(CDCl$_3$) includes 0.71 (d,7 Hz,3H), 0.95 (d,6 Hz,3H), 1.06 (d,6 Hz,3H), 1.42 (s,9H), 1.88 (s,3H), 2.05 (s,3H), 3.10 (m,1H), 3.96 (d,6 Hz,1H), 4.29 (t,6 Hz,1H), and 4.91 (q,3 Hz,1H), from the product of Example 14 (76 mg).

EXAMPLE 18

12-Demethyl-23-desoxy-Factor A 5-acetate 12-carboxylic acid, methyl ester

To a stirred solution of the product of Example 9 (50 mg) in toluene (2 ml), under nitrogen, was added oxalyl chloride (13 µl). After 90 min the solution was added over 2 min to a refluxing mixture of 2-mercaptopyridine N-oxide sodium salt (33.5 mg), trityl thiol (83 mg) and 4-dimethylaminopyridine (2 mg) in toluene (3 ml). After 2¼ h the solution was cooled, diluted with ethyl acetate (30 ml) and washed with 2N hydrochloric acid, sodium bicarbonate, water and brine. Drying and evaporation of the organic phase gave a foam which was purified by flash chromatography over silica (36 g), using hexane:ethyl acetate (3:1) as eluent, to give the title compound (20 mg) as a white foam, $[\alpha]_D^{21}+35°$ (c 0.4, CHCl$_3$), $\lambda_{max}^{EtOH}$ 245 nm ($\epsilon$max 25,700), $\nu$max (CHBr$_3$) 1735 cm$^{-1}$ (acetate and CO$_2$R), $\delta$(CDCl$_3$) includes 0.70 (d,5 Hz,3H), 0.92 (d,6 Hz,3H), 1.02 (d,6 Hz,3H), 1.75 (s,3H), 2.16 (s,3H), 3.22 (m,1H), 3.67 (s,3H), 4.05 (d,5 Hz,1H), 5.52 (m,2H).

EXAMPLE 19

12-Demethyl-23-desoxy-Factor A 12-carboxylic acid, methyl ester

To a cold (0° to 5°) solution of the product of Example 18 (30 mg) in methanol (1 ml) was added aqueous 1N sodium hydroxide (48 µl). After 5 h the solution was diluted with ether (40 ml) and washed with 2N hydrochloric acid (20 ml), water and brine. Drying and evaporation of the organic phase gave a foam which was purified by chromatography over silica (16 g) to yield the title compound (19 mg), $[\alpha]_D^{21}+41°$ (c 0.2, CHCl$_3$), $\lambda_{max}^{EtOH}$ 245.4 nm ($\epsilon$max 22,500), $\nu$max (CHBr$_3$) 3540 (OH), 3450 (OH), and 1720 cm$^{-1}$ (CO$_2$R), $\delta$(CDCl$_3$) includes 0.69 (d,5 Hz,3H), 0.93 (d,6 Hz,3H), 1.03 (d,6 Hz,3H), 1.87 (s,3H), 3.26 (m,2H), 3.68 (s,3H), 3.96 (d,6 Hz,1H), and 4.29 (t,6 Hz,1H).

EXAMPLE 20

12-Demethyl-23-keto-Factor A 5-acetate 12-carboxylic acid, methyl ester

A solution of the product of Example 9 may be oxidised with pyridinium dichromate using the method described in Example 70 in UK Patent Specification 2176182. The residue purified by chromatography over a column of Merck Kieselgel 60,230–400 mesh, eluting with hexane:ethyl acetate (2:1) affords the title compound $\lambda_{max}^{EtOH}$ 245.6 nm ($\epsilon$max 25,200) $\nu$max (CHBr$_3$) 3450 (weak OH), 1724 (ketone and lactone) and 1232 cm$^{-1}$ (acetate), $\delta$(CDCl$_3$) includes 0.86 (d,6 Hz,3H), 0.97 (d,6 Hz,3H), 1.07 (d,6 Hz,3H), 1.76 (s,3H), 2.16 (s,3H), 2.50 (s,2H), 3.23 (m,1H), 4.06 (d,6 Hz,1H), and 5.53 (m,2H).

EXAMPLE 21

12-Demethyl-23[E]-methoxyimino-Factor A 12-carboxylic acid, methyl ester

A solution of Example 3 (40 mg) in ether (3 ml) was cooled to ca 10° and treated with ethereal diazomethane (1.5 ml). After 15 min, excess diazomethane was destroyed with acetic acid and the resulting colourless solution was evaporated to a foam. The foam was purified by flash chromatography over silica (20 g) using dichloromethane:acetone (20:1) as eluent. Appropriate fractions were combined and evaporated to give the title compound (39 mg) as a white foam, $[\alpha]_D^{21}+41°$ (c 0.4, CHCl$_3$), $\lambda_{max}^{EtOH}$ 245.6 nm ($\epsilon$max 23,200), $\nu$max (CHBr$_3$) 3540 (OH), 3450 (OH) and 1720 cm$^{-1}$ (lactone), $\delta$(CDCl$_3$) includes 0.91 (d,6 Hz,3H), 0.96 (d,6 Hz,3H), 1.06 (d,6 Hz,3H), 1.88 (s,3H), 3.2–3.4 (m,3H), 3.66 (s,3H), 3.83 (s,3H), 3.96 (d,6 Hz,1H), and 4.29 (t,6 Hz,1H).

EXAMPLE 22

12-Demethyl-23[E]-methoxyimino-Factor A 12-carboxylic acid, n-butyl amide

To a solution of Example 3 (84 mg) in dichloromethane (0.3 ml) was added a solution of 1-ethoxycarbonyl-2-ethoxy-1,2-dihydroquinoline (31 mg) in dichloromethane (0.5 ml) followed by n-butylamine (12.5 µl) in dichloromethane (0.5 ml). After 96 h dichloromethane was added and the solution was washed with 2N hydrochloric acid (2×20 ml), water (20 ml) and brine. The dried organic phase was evaporated to leave a powder which was purified by medium pressure chromatography over silica (30 g) using dichloromethane:ethyl acetate (6:1) as eluent. Appropriate fractions were combined and evaporated to give the title compound (58 mg) as a white powder, $[\alpha]_D^{21}+68°$ (c 0.5, CH$_2$Cl$_2$), $\lambda_{max}^{EtOH}$ 248 nm ($\epsilon$max 29,000), $\nu$max (CHBr$_3$) 3550 (OH), 3420 (NH), 1708 (lactone) and 1658 and 1510 c$^{-1}$ (CONH), $\delta$(CDCl$_3$) includes 0.92 (d,6 Hz,3H), 0.99 (d,6 Hz,3H), 1.08 (d,6 Hz,3H), 0.92 (m,3H), 1.90 (s,3H), 3.09 (m,1H), 3.29 (d,14 Hz,1H), 3.20 (m,2H), 3.86 (s,3H), 4.00 (d,6 Hz,1H), and 4.32 (t,6 Hz,1H).

The following are examples of formulations according to the invention. The term 'Active Ingredient' as used hereinafter means a compound of the invention.

MULTIDOSE PARENTERAL INJECTION

| | Example 1 | |
|---|---|---|
| | % w/v | Range |
| Active ingredient | 2.0 | 0.1–6.0% w/v |
| Benzyl alcohol | 1.0 | |
| Polysorbate 80 | 10.0 | |
| Glycerol formal | 50.0 | |
| Water for Injections | to 100.0 | |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

| | Example 2 | |
|---|---|---|
| | % w/v | Range |
| Active ingredient | 4.0 | 0.1–7.5% w/v |
| Benzyl alcohol | 2.0 | |
| Glyceryl triacetate | 30.0 | |
| Propylene glycol | to 100.0 | |

Dissolve the active ingredient in the benzyl alcohol and glyceryl triacetate. Add the propylene glycol and make up to volume. Sterilize the product by conventional pharmaceutical methods, for example sterile filtration, and package aseptically.

| Example 3 | | |
| --- | --- | --- |
| | % | Range |
| Active ingredient | 2.0 w/v | 0.1–7.5% w/v |
| Ethanol | 36.0 w/v | |
| Non-ionic surfactant | 10.0 w/v | |
| (e.g. Synperonic PE L44*) | | |
| Propylene glycol | to 100.0 | |

Dissolve the active ingredient in the ethanol and surfactant and make up to volume. Sterilize the product by conventional pharmaceutical methods, for example sterile filtration, and package aseptically.

| Example 4 | | |
| --- | --- | --- |
| | % | Range |
| Active Ingredient | 2.0 w/v | 0.1–3.0% w/v |
| Non-ionic surfactant | 2.0 w/v | |
| (e.g. Synperonic PE F68*) | | |
| Benzyl alcohol | 1.0 w/v | |
| Miglyol 840** | 16.0 w/v | |
| Water for Injections | to 100.0 | |

*Trademark of ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

| Aerosol spray | | |
| --- | --- | --- |
| | % w/w | Range |
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet | |
| --- | --- |
| Method of manufacture - wet granulation | |
| | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose | to tablet core weight of 450 mg |

Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use | |
| --- | --- |
| Method of manufacture - dry granulation | |
| | mg |
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

| Veterinary intrammary injection | | |
| --- | --- | --- |
| | mg/dose | Range |
| Active Ingredient | | 150 mg | 0.05–1.0 g |
| Polysorbate 60 | 3.0% w/w | | |
| White Beeswax | 6.0% w/w | } to 3 g | } to 3 or 15 g |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary slow-release bolus | | |
| --- | --- | --- |
| | % w/w | Range |
| Active Ingredient | | 0.25–2 g |
| Colloidal silicon dioxide | 2.0 | } to required fill weight |
| Microcrystalline cellulose | to 100.0 | |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient.

| Veterinary oral drench | | |
| --- | --- | --- |
| | % w/v | Range |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | | |
|---|---|---|
| | % w/w | Range |
| Active Ingredient | 4.0 | 1–20% w/w |
| Saccharin sodium | 2.5 | |
| Polysorbate 85 | 3.0 | |
| Aluminium distearate | 5.0 | |
| Fractionated coconut oil | to 100.0 | |

Disperse the aluminium distearate in the fractionated coconut oil and polysorbate 85 by heating. Cool to room temperature and disperse the saccharin sodium in the oily vehicle. Disperse the active ingredient in the base. Fill into plastic syringes.

| Granules for veterinary in-feed administration | | |
|---|---|---|
| | % w/w | Range |
| Active Ingredient | 2.5 | 0.05–5% w/w |
| Calcium sulphate, hemi-hydrate | to 100.0 | |

Blend the Active Ingredient with the calcium sulphate. Prepare the granules using a wet granulation process. Dry using a tray or fluid-bed drier. Fill into the appropriate container.

| Veterinary Pour-on | | |
|---|---|---|
| | % w/v | Range |
| Active Ingredient | 2.0 | 0.1 to 30% |
| Dimethyl sulphoxide | 10.0 | |
| Methyl Isobutyl ketone | 30.0 | |
| Propylene glycol (and pigment) | to 100.0 | |

Dissolve the active ingredient in the dimethyl sulphoxide and the methyl isobutyl ketone. Add the pigment and make up to volume with the propylene glycol. Fill into the pour-on container.

| Emulsifiable Concentrate | |
|---|---|
| Active ingredient | 50 g |
| Anionic emulsifier | 40 g |
| (e.g. Phenyl sulphonate CALX) | |
| Non-ionic emulsifier | 60 g |
| (e.g. Synperonic NP13)* | |
| Aromatic solvent (e.g. Solvesso 100) | to 1 liter. |

*Trademark of ICI

Mix all ingredients, stir until dissolved.

| Granules | |
|---|---|
| (a) Active ingredient | 50 g |
| Wood resin | 40 g |
| Gypsum granules (20–60 mesh) | to 1 kg |
| (e.g. Agsorb 100A) | |
| (b) Active ingredient | 50 g |
| Synperonic NP13* | 40 g |
| Gypsum granules (20–60 mesh) | to 1 kg. |

*Trademark of ICI

Dissolve all ingredients in a volatile solvent e.g. methylene chloride, add to granules tumbling in mixer. Dry to remove solvent.

We claim:

1. Compounds of formula (1)

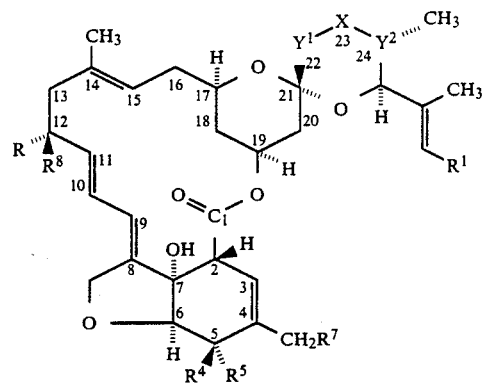

and salts thereof, wherein $R^1$ represents a methyl, ethyl or isopropyl group;
$Y^1$ is $-CH_2-$; $Y^2$ is $-CH-$ and X represents

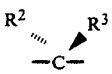

wherein $R^2$ represents a hydrogen atom or a group $OR^8$ wherein $OR^8$ is a hydroxyl group or a substituted hydroxyl group having up to 25 carbon atoms, and $R^3$ represents a hydrogen atom, or $R^2$ and $R^3$ together with the carbon atom to which they are attached represent $>C=O$, $>C=CH_2$ or $>C=NOR^9$, wherein $R^9$ represents a hydrogen atom, a $C_{1-8}$ alkyl group or a $C_{3-8}$ alkenyl group, and the group $>C=NOR^9$ is in the E configuration, or $-Y^1-X-Y^2-$ represents $-CH=CH-CH-$ or $-CH_2-CH=C-$;

$R^4$ represents a group $OR^8$ as defined above and $R^5$ represents a hydrogen atom, or $R^4$ and $R^5$ together with the carbon atom to which they are attached represent $>C=O$ or $>C=NOR^{9a}$, wherein $R^{9a}$ is as defined above for $R^9$;

$R^6$ represents a hydrogen atom and R represents $-CH_2OH$, $-CHO$, $-CO_2H$ or a carboxylic acid ester or amide group; or $R^6$ represents a hydroxyl group and R represents a methyl group; and $R^7$ represents a hydrogen atom or when R represents a group $-CH_2OH$ then $R^7$ may also represent a hydroxy group;

$R^8$ of the substituted hydroxy group is selected from the group consisting of:
an acyl group having the formula $R^{10}CO-$ or $R^{10}OCO-$ or $R^{10}OCS-$;
a formyl group;
a group $R^{11}$ wherein $R^{11}$ is a cycloalkyl substituted alkyl or a group $R^{10}$;
a group $R^{12}SO_2-$ wherein $R^{12}$ is a $C_{1-4}$ alkyl or a $C_{1-6}$ aryl group;
a silyl group;
a cyclic or acyclic acetal group;
a group $-CO(CH_2)_nCO_2R^{13}$ wherein $R^{13}$ is a hydrogen atom or a group $R^{10}$ and n represents 0, 1 or 2;
a group $R^{14}R^{15}NCO-$ wherein $R^{14}$ and $R^{15}$ each independently represent a hydrogen atom or a $C_{1-4}$ alkyl group;

$R^{10}$ is selected from the group consisting of alkyl, alkenyl, alkynyl, cycloalkyl, aryl, halogen substituted alkyl, carboxy substituted alkyl, $C_{1-4}$ alkoxy substituted alkyl, phenoxy substituted alkyl, and silyloxy substituted alkyl;

said carboxylic acid ester having the formula $-CO_2R^{16}$;

wherein $R^{16}$ is selected from the group consisting of alkyl, alkenyl, alkynyl, cycloalkyl, aralkyl, aryl, halogen substituted alkyl, carboxy substituted alkyl, $C_{1-4}$ alkoxy substituted alkyl, phenoxy substituted alkyl, and silyloxy substituted alkyl;

and said carboxylic acid amide having the formula:

$-CONR^{17}R^{18}$;

wherein $R^{17}$ and $R^{18}$ each independently represent a hydrogen atom or a group $R^{16}$.

2. Compounds according to claim 1 in which $R^1$ is an isopropyl group.

3. Compounds according to claim 1 in which R is $-COOR^{16}$ where $R^{16}$ is a $C_{1-8}$ alkyl group or $-CONHR^{18}$ where $R^{18}$ is a $C_{1-8}$ alkyl group.

4. Compounds according to claim 1 in which $Y^1$ is $-CH_2-$, $Y^2$ is $-CH-$ and X is $-C(R^2)(R^3)-$, where $R^2$ is a hydrogen atom or a hydroxy, ethoxy or acetyloxy group and $R^3$ is a hydrogen atom, or $R^2$ and $R^3$ together with the carbon atom to which they are attached represent $>C=O$, $>C=CH_2$ or $>C=NOCH_3$; and $R^4$ is a hydroxy, methoxy or acetyloxy group or $R^4$ and $R^5$ together with the carbon atom to which they are attached represent $>C=NOCH_3$.

5. Compounds according to claim 1 in which R is $-COOH$.

6. Compounds according to claim 1 in which:

R is $-CO_2CH_3$, $R^1$ is an isopropyl group, $Y^1$ is $-CH_2-$, $Y^2$ is $-CH-$, X is $>C=NOCH_3$, $R^4$ is a hydroxyl group and $R^5$ is hydrogen atom; or R is $-CONH(CH_2)_3CH_3$, $R^4$ is an isopropyl group, $Y^1$ is $-CH_2-$, $Y^2$ is $-CH-$, X is $>C=NOCH_3$, $R^4$ is a hydroxyl group and $R^5$ is a hydrogen atom; or R is $-CO_2H$, $R^1$ is an isopropyl group, $Y^1$ is $-CH_2-$, $Y^2$ is $-CH-$, X is $>C=NOCH_3$, $R^4$ is a hydroxy group and $R^5$ is a hydrogen atom.

7. A pharmaceutical composition containing a pesticidally effective amount of at least one compound as claimed in claim 1 together with a pharmaceutically acceptable carrier.

8. A veterinary composition containing a pesticidally effective amount of at least one compound as claimed in claim 1 and a veterinary acceptable carrier.

9. A pesticidal composition containing a pesticidally effective amount of a compound as claimed in claim 1 and a pesticidally acceptable carrier.

10. A method of controlling insect, acarine or nematode pests which comprises applying an amount of a compound according to claim 1 effective in combatting pests to the pests to a locus of said pests.

* * * * *